United States Patent [19]

Pensak

[11] 4,152,419

[45] May 1, 1979

[54] DENTIFRICE COMPOSITION

[75] Inventor: Philip Pensak, New Brunswick, N.J.

[73] Assignee: Colgate-Palmolive Company, New York, N.Y.

[21] Appl. No.: 800,267

[22] Filed: May 25, 1977

[51] Int. Cl.² .......................... A61K 7/18; A61K 7/16
[52] U.S. Cl. .......................................... 424/52; 424/57
[58] Field of Search ...................................... 424/52, 57

[56] References Cited

U.S. PATENT DOCUMENTS

| | | | |
|---|---|---|---|
| 3,119,743 | 1/1964 | Ericsson | 424/52 |
| 3,227,617 | 1/1966 | Manahan et al. | 424/52 |
| 3,227,618 | 1/1966 | Manahan et al. | 424/52 |
| 3,911,104 | 10/1975 | Harrison | 424/52 |
| 3,927,202 | 12/1975 | Harvey et al. | 424/57 |
| 4,064,231 | 12/1977 | Asakawa et al. | 424/52 |

FOREIGN PATENT DOCUMENTS 1435624  11/1974  United Kingdom ...................... 424/52

Primary Examiner—Delbert R. Phillips
Attorney, Agent, or Firm—Robert L. Stone; Murray M. Grill; Herbert S. Sylvester

[57] ABSTRACT

Dentifrice composition containing an alkali monofluorophosphate and an alkali metal fluoride and a polishing material which consists essentially of a water-insoluble phosphate salt, at least a major portion of which is an insoluble alkali metal metaphosphate.

7 Claims, No Drawings

DENTIFRICE COMPOSITION

Dentifrice compositions containing a fluorine providing component and a compatible polishing material have been widely used to reduce caries formation while polishing and cleaning teeth. It has been desirable that the polishing material be compatible with the fluorine-providing material so that optimum amounts of soluble fluoride can remain available in the dentifrice from the time it is prepared until it is used.

Alkali metal monofluorophosphate such as potassium monofluorophosphate and particularly sodium monofluorophosphate are excellent in the reduction of caries as fluorine-providing materials. Sodium monofluorophosphate has been used successfully in commercial dentifrices. It is compatible to varying degrees with a limited number of polishing agents, such as insoluble alkali metal (e.g., sodium) metaphosphate, dicalcium phosphate and calcium carbonate. It is used in any suitable purity provided that any impurities do not substantially adversely affect the desired properties. In general, the purity is desirably at least about 80%. For best results it should be at least 85%, and preferably at least 90% by weight of sodium monofluorophosphate with the balance being primarily impurities or by-products of manufacture such as sodium fluoride, water-soluble sodium phosphate salt, and the like. Expressed in another way, the sodium monofluorophosphate employed should have a total fluoride content of about 12%, preferably above 12.7%; a content of not more than 1.5%, preferably not more than 1.2% of free sodium fluoride; and a sodium monofluorophosphate content of at least 12%, preferably at least 12.1%, all calculated as fluorine.

Alkali metal fluorides such as sodium fluoride and potassium fluoride have also been proposed as anti-caries fluorine-providing materials. Indeed, sodium fluoride has been used commercially in dentifrices.

Occasionally, there have been proposals to use a plurality of fluorine-providing materials, for example a monofluorophosphate and a simple fluoride, the simple fluoride being in excess of that inherently present in the monofluorophosphate. This has been limited by the fact that compatibility factors between a particular polishing material and a monofluorophosphate and the same polishing material and a simple fluoride may be substantially different. Nevertheless, a dentifrice comprising sodium fluoride and sodium monofluorophosphate, with the fluoride providing 40–80% of the total fluoride and the monofluorophosphate providing 20–60% of the total fluoride has been described in British Patent Specification No. 1,435,624; the polishing material therein being calcium carbonate alone or mixed with other polishing agents such as water-insoluble sodium or potassium metaphosphate, hydrated or or anhydrous dicalcium phosphate, calcium pyrophosphate, zirconium silicate and others. Similar dentifrices containing sodium monofluorophosphate, sodium fluoride and calcium carbonate are described in the Journal of the Society of Cosmetic Chemistry, Vol. 25, pages 3–11, 1974.

The present invention provides for the use of a polishing material which consists essentially of a water-insoluble phosphate salt, at least a major portion of which is an insoluble alkali metal metaphosphate in a dentifrice vehicle containing an alkali metal monofluorophosphate and an alkali metal fluoride in amount to provide a total fluoride content of about 0.01–1.5% by weight to the dentifrice, the weight ratio of fluoride from the alkali metal monofluorophosphate to the fluoride from the alkali metal fluoride being about 10:1 to about 1:10.

It is important to the invention that the polishing material include a major amount of insoluble alkali metal metaphosphate. Moreover, the polishing material should consist essentially of water-insoluble phosphate salt and therefore not included a polishing agent such as calcium carbonate. Calcium carbonate would substantially reduce the retention of soluble fluoride from the fluorine-providing compounds of the dentifrice when the polishing material is mainly an insoluble alkali metal metaphosphate.

An advantage of this invention lies in the provision of superior retention of monofluorophosphate as fluoride by the dentifrice. Other advantages will be apparent from consideration of the disclosure.

Sodium monofluorophosphate and potassium monofluorophosphate can be used as the alkali metal monofluorophosphate. Sodium monofluorophosphate is preferred. The alkali metal monofluorophosphate is used in amount providing about 0.01–1% by weight fluorine in the dentifrice. This corresponds to about 0.076–7.6% by weight of sodium monofluorophosphate. About 0.38–1.14% of sodium monofluorophosphate is preferred.

Sodium fluoride and potassium fluoride can be used as the alkali metal fluoride. Sodium fluoride is preferred. The alkali metal fluoride is used in amount providing about 0.005–0.5% by weight fluorine in the dentifrice. This corresponds to about 0.011–1.1% by weight of sodium fluoride. About 0.06–0.11% of sodium fluoride is preferred. The weight ratio of fluoride from the alkali metal monofluorophosphate to the fluoride from the alkali metal fluoride in the dentifrice as formulated is about 10:1 to about 1:10, preferably about 3:1 to about 1:1, such as about 3:1, about 2:1 and about 1:1.

The polishing material contains wholly or at least as its major component a water-insoluble alkali metal metaphosphate. The insoluble alkali metal metaphosphates are typically the insoluble sodium and potassium salts of polymetaphosphoric acid. The insoluble sodium metaphosphate is preferred. These materials are known in the art with the insoluble sodium metaphosphate having been suggested as a polishing agent as previously indicated. Such materials may be formed in any suitable manner, as illustrated by Thorpe's Dictionary of Applied Chemistry, Vol. 9 (4th ed.), pages 510–511. The forms of insoluble sodium metaphosphate known as Madrell's salt and Kurrol's salt are further examples of suitable materials. These metaphosphate salts exhibit only a minute solubility in water, and are commonly referred to as insoluble metaphosphates. There is present a minor amount of soluble phosphate material as impurities, usually of the order of a few percent such as up to about 4% by weight. The amount of soluble phosphate material which is believed to be a soluble sodium trimetaphosphate in the case of insoluble sodium metaphosphate may be reduced by washing with water if desired. The insoluble alkali metal metaphosphate is typically employed in powder from of a size such that no more than about 1% of the material is larger than about 37 microns.

The polishing material amounts to about 20–95% by weight of the dentifrice; typically about 20–75% when the dentifrice is a toothpaste and about 70–95% when it is a tooth powder. Preferably, the insoluble alkali metal metaphosphate is the only polishing agent employed.

However, other water-insoluble phosphate salts may be included as minor components (less than 50% by weight of the polishing material), typically about 5-20% by weight of the polishing material. Such other salts include dicalcium phosphate (anhydrous and dihydrate), dimagnesium phosphate (anhydrous and trihydrate), tricalcium phosphate and calcium pyrophosphate. When employed, dicalcium phosphate is preferred. The minor polishing agent when present is preferably in amount up to about 12% by weight of the total polishing material.

It is noted that a minor amount such as about 0.5-10% by weight of the dentifrice, typically about 1%, of the insoluble non-phosphate polishing agent hydrated aluminum oxide may be present. Its presence provides a substantial additional effect to the dentifrice other than its minor contribution to polishing effect. It inhibits or even eliminates the tendency of the dentifrice, when it is a toothpaste, to separate or "bleed" in its tube.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or actionic in structure. It is usually preferred to use the water-soluble non-soap or synthetic organic detergents. Suitable detersive materials are known and include, for example, the water-soluble salts of higher fatty acid monoglyceride monosulfate detergent (e.g., sodium coconut fatty acid monoglyceride monosulfate), higher alkyl sulfate (e.g., sodium lauryl sulfate), alkyl aryl sulfonate (e.g., sodium dodecyl benzene sulfonate, higher fatty acid esters of 1,2-dihydroxy propane sulfonate) and the like.

The various surface active materials may be used in any suitable amount, generally from about 0.05 to about 10% by weight, and preferably from about 0.5 to 5% by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

In the preparation of tooth powders, it is usually sufficient to admix mechanically, for example, by milling, the various solid ingredients, in appropriate quantities and particle sizes.

In dental cream formulations, the liquids and solids should be proportioned to form an extrudable creamy mass of desirable consistency. In general, liquids in the dental cream will comprise chiefly water, glycerine, sorbitol, propylene glycol, or the like, including suitable mixtures thereof. It is advantageous usually to use a mixture of both water and a humectant or binder such as glycerine or sorbitol. It is preferred to use glycerine. The total liquid content will generally be about 20-75% by weight of the formulation. It is preferred to use also a gelling agent in dental creams such as the natural and synthetic gum and gum-like material, e.g., Irish moss, gum tragacanth, sodium carboxymethylcellulose, polyvinylpyrroilidone, starch and the like. The Irish moss and sodium carboxymethylcellulose are compatible particularly and are preferred gelling agents as illustrated. The gum content is usually in an amount up to about 10% and preferably about 0.5-5% by weight of the formulation.

Various other materials may be incorporated in the oral preparations of this invention. Examples thereof are coloring or whitening agents, preservatives, silicones, chlorophyll compounds and ammoniated materials such as urea, diammonium phosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavoring or sweetening materials may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No.

3,932,606. Suitably, flavor and sweetening agent may together comprise from about 0.01 to 5% or more of the instant invention.

The dental creams should have a pH practicable for use. A pH range of 5 to 9 is particularly desirable. The reference to the pH is meant to be the pH determination directly on the toothpaste. If desired, materials such as benzoic acid or citric acid may be added to adjust the pH to say 5.5 to 6.5.

The dentifrice is typically packaged in an extrudible tube, typically lined aluminum or lead or in a pressurized container.

The following specific examples are further illustrative of the nature of the present invention, but it is to be understood that the invention is not limited thereto. The compositions are prepared in the usual manner and all amounts of the various ingredients are by weight unless otherwise specified.

EXAMPLE 1

The following toothpaste dentifrices are prepared, deaerated and tubed in plastic inner lined aluminum tubes.

| Components | Parts A | B | C | D |
|---|---|---|---|---|
| Glycerine | 10 | 10 | 10 | 10 |
| Sorbitol (70%) | 17 | 17 | 17 | 17 |
| Sodium Carboxymethylcellulose | 0.9 | 0.9 | 0.9 | 0.9 |
| Sodium benzoate | 0.5 | 0.5 | 0.5 | 0.5 |
| Sodium saccharin | 0.2 | 0.2 | 0.2 | 0.2 |
| Sodium monofluorophosphate | 0.76 | 0.76 | 0.38 | 0.57 |
| Sodium fluoride | — | 0.11 | 0.11 | 0.06 |
| Titanium dioxide | 0.4 | 0.4 | 0.4 | 0.4 |
| Sodium lauryl sulfate | 1.5 | 1.5 | 1.5 | 1.5 |
| Water (distilled) | 19.89 | 19.78 | 20.16 | 20.02 |
| Insoluble sodium metaphosphate | 47.85 | 47.85 | 47.85 | 47.85 |
| Flavor | 1 | 1 | 1 | 1 |
| pH | 5.8 | 5.8 | 5.8 | 5.8 |

Control dentifrice A in which sodium monofluorophosphate is the only fluorine source contains a theoretical amount of 0.1% monofluorophosphate as fluoride; Dentifrice B contains a theoretical amount of 0.1% monofluorophosphate as fluoride; Dentifrice C contains a theoretical amount of 0.05% monofluorophosphate as fluoride; and Dentifrice D contains a theoretical amount of 0.075% monofluorophosphate as fluoride.

Monofluorophosphate as fluoride levels are determined initially and after aging for nine weeks at 49° C. accelerated aging as follows:

| Toothpaste | Theoretical Amount | Initial | 9 Weeks 49° C. |
|---|---|---|---|
| A | 0.1% | 0.091% | 0.087% |
| B | 0.1% | 0.093% | 0.104% |
| C | 0.05% | 0.044% | 0.062% |
| D | 0.075% | 0.071% | 0.073% |

Thus, it is seen that the presence of sodium fluoride in toothpastes B, C and D substantially increases the retention of monofluorophosphate as fluoride, even to levels beyond that theoretically expected from the amount of sodium monofluorophosphate employed, 95.6% of the initially determined monofluorophosphate as fluoride is found in control toothpaste A after nine weeks at 49° C., while 111.8%, 140.9% and 102.8% respectively are found in toothpaste B, C and D.

EXAMPLE 2

Each of the toothpaste dentifrices of Example 1 are modified by replacing six parts of insoluble sodium metaphosphate with five parts of anhydrous dicalcium phosphate and one part of alpha-alumina trihydrate to form respectively control toothpaste A' having a pH of 6.0; and toothpaste B' having a pH of 6.1, C' having a pH of 6.1 and D' having a pH of 6.1.

The retentions of monofluorophosphate as fluoride are indicated below:

| Toothpaste | Theoretical Amount | Initial | 9 Weeks- 49° C. |
|---|---|---|---|
| A' | 0.1% | 0.098% | 0.064% |
| B' | 0.1% | 0.099% | 0.085% |
| C' | 0.05% | 0.045% | 0.040% |
| D' | 0.075% | 0.075% | 0.052% |

Thus, it is seen that the presence of sodium fluoride in toothpastes B', C' and D' substantially increases the retention of monofluorophosphate as fluoride. 65.3% of the initially determined monofluorophosphate as fluoride is found in control toothpaste A' after nine weeks at 49° C., while 85.9%, 88.9% and 69.3% respectively are found in toothpastes B', C' and D'.

By way of further comparison toothpastes similar in formulation to toothpaste C (with 0.38 parts of sodium monofluorophosphate and 0.11 parts of sodium fluoride) are prepared, but including insoluble sodium metaphosphate and calcium carbonate in the following amounts:

|  | Toothpaste E |
|---|---|
| Insoluble sodium metaphosphate | 42.85 |
| Calcium carbonate | 5 |

The following retention levels of monofluorophosphate as fluoride are observed:

| Toothpaste | Theoretical Amount | Initial | 9 Weeks- 49° C. |
|---|---|---|---|
| E | 0.05% | 0.046% | 0.008% |

Thus, it is seen that when insoluble sodium metaphosphate is the main polishing agent, but the insoluble polishing material calcium carbonate is also present in substantial amount, poor retention of monofluorophosphate as fluoride occurs.

It will be apparent to one skilled in the art that modifications of dentifrices B, C, D, B', C' and D' may be made.

I claim:

1. A dental cream composition free of calcium carbonate comprising a polishing material which consists essentially of a water-insoluble phosphate salt, at least a major portion of which is an insoluble sodium metaphosphate in a dentifrice vehicle containing an alkali metal monofluorophosphate and an alkali metal fluoride in amount to provide a total fluoride content of about 0.01-1.5% by weight to the dentifrice, the weight ratio of fluoride from the alkali metal monofluorophosphate to the fluoride from the alkali metal fluoride being about 10:1 to about 1:10.

2. The dental cream composition claimed in claim 1 wherein said weight ratio of fluoride from the alkali metal monofluorophosphate to the fluoride from the alkali metal fluoride is about 3:1 to about 1:1.

3. The dental cream composition claimed in claim 2 wherein said polishing material is present in amount of about 20-75% by weight.

4. The dental cream composition claimed in claim 2 wherein said polishing material consists essentially of a major amount of insoluble sodium metaphosphate and a minor amount of dicalcium phosphate.

5. The dental cream composition claimed in claim 4 wherein said dicalcium phosphate is present in amount of about 5-20% by weight of the polishing material.

6. The dental cream composition claimed in claim 2 wherein said alkali metal monofluorophosphate is sodium monofluorophosphate and said alkali metal fluoride is sodium fluoride.

7. The dental cream composition claimed in claim 6 wherein said sodium monofluorophosphate is present in amount of about 0.38-1.14% by weight and said sodium fluoride is present in amount of about 0.06-0.11% by weight.

* * * * *